(12) United States Patent
Huotari et al.

(10) Patent No.: US 8,292,618 B2
(45) Date of Patent: Oct. 23, 2012

(54) DENTAL UNIT AND METHOD FOR FEEDING WATER

(75) Inventors: Arto Huotari, Helsinki (FI); Arto Virta, Helsinki (FI)

(73) Assignee: Planmeca Oy, Helsinki (FI)

( * ) Notice: Subject to any disclaimer, the term of this patent is extended or adjusted under 35 U.S.C. 154(b) by 1303 days.

(21) Appl. No.: 10/575,956

(22) PCT Filed: Oct. 15, 2004

(86) PCT No.: PCT/FI2004/000616
§ 371 (c)(1),
(2), (4) Date: Nov. 21, 2006

(87) PCT Pub. No.: WO2005/037125
PCT Pub. Date: Apr. 28, 2005

(65) Prior Publication Data
US 2007/0111157 A1    May 17, 2007

(30) Foreign Application Priority Data
Oct. 15, 2003 (FI) .......... 20031510

(51) Int. Cl.
*A61G 17/02* (2006.01)
(52) U.S. Cl. .......... 433/80
(58) Field of Classification Search .......... 433/80–81, 433/98, 215, 229; 601/162–165; 417/415, 417/423.1–423.14, 118
See application file for complete search history.

(56) References Cited

U.S. PATENT DOCUMENTS

| | | | | |
|---|---|---|---|---|
| 3,014,620 A | * | 12/1961 | Moore | 222/642 |
| 3,053,435 A | * | 9/1962 | Sanders et al. | 417/403 |
| 3,363,570 A | * | 1/1968 | Scott | 417/36 |
| 4,021,921 A | * | 5/1977 | Detaille | 433/81 |
| 4,668,190 A | * | 5/1987 | Overmyer | 433/80 |
| 5,046,950 A | * | 9/1991 | Favonio | 433/81 |
| 5,151,731 A | * | 9/1992 | Yamada et al. | 396/626 |
| 5,295,829 A | * | 3/1994 | Frey et al. | 433/82 |
| 5,318,443 A | * | 6/1994 | Overmyer | 433/104 |
| 5,431,861 A | * | 7/1995 | Nagahiro et al. | 261/140.1 |
| 5,558,841 A | * | 9/1996 | Nakagawa et al. | 422/105 |
| 5,785,523 A | * | 7/1998 | Overmyer | 433/82 |
| 6,179,613 B1 | * | 1/2001 | Yang | 433/80 |
| 6,224,378 B1 | * | 5/2001 | Valdes et al. | 433/224 |
| 6,250,920 B1 | * | 6/2001 | Overmyer | 433/80 |
| 6,482,370 B2 | * | 11/2002 | Holsclaw et al. | 422/186.12 |

* cited by examiner

*Primary Examiner* — Cris L Rodriguez
*Assistant Examiner* — Hao D Mai
(74) *Attorney, Agent, or Firm* — Stites & Harbison PLLC; Juan Carlos A. Marquez, Esq.

(57) ABSTRACT

The invention relates to a dental unit and a method for feeding water to instruments and/or to other water outlet points of a dental unit. The object of the invention is to enable keeping pressure of the water lines of a dental unit essentially stable, especially also when the relatively stable pressure typical for public water systems cannot be taken advantage of because of potential backflow of water contaminated at the point of use to the public water system. According to the invention there is arranged a pressure chamber (12) to the feed water line (10) of a dental unit, the said pressure chamber (12) being arranged in functional connection with pressure control means (14, 15), and upstream of the said pressure chamber (12) a pump (13), which is arranged to be able to pump water to the said pressure chamber (12) also when it is pressurized.

24 Claims, 3 Drawing Sheets

DENTAL UNIT AND METHOD FOR FEEDING WATER

BACKGROUND OF THE INVENTION

The invention relates to a dental unit according to preamble of the following patent claim 1 and a method according to preamble of the following patent claim 14 for feeding water to instruments of a dental unit and/or to other water outlet points of a dental unit.

In dental units there is typically used as feed water either water treated separately outside the system or the unit is connected to a public water system. With respect to the latter, orders of the authorities in numerous countries specify various criteria e.g. in relation to how connection to the water system needs to be arranged in order to prevent water that may get contaminated at the point of use flowing backwards to the water system. One such order of the authorities requires arranging a reservoir basin open to atmospheric pressure and the feed link of the water system at a distance from each other, i.e. in practise, physical separation of the feed water line of a dental unit from the water system.

According to typical prior art technology, uncontrolled pressure alterations in the water lines is a problem of many of the feed water arrangements of dental units, which can cause leakages in valves or gaskets, annoying splattering at the water outlet points of the dental unit, breaking of the pressure sensors and in some cases even hampering operation of the dental instruments. Special attention must be paid to controlling the pressure of the feed water line when the public water system is used as the water source but the feed water line is physically separated from the water system, e.g. due to the orders of the authorities as discussed above, in which case the relatively stable pressure typical for a public water system cannot be taken advantage of. Such a basic solution has been described e.g. in a U.S. Pat. No. 5,039,405, and one such kind of an application for re-pressurizing the feed water in an EP patent publication 0 524 344 B2, having been granted in modified form after an appeal. With a solution according to that EP patent, i.e. parallel use of two pumps of a specific construction, it is possible to keep pressure of the instrument water lines fairly stable, but with respect to automatic control engineering the arrangement is somewhat complicated and also comprises of quite a number of moving parts.

SUMMERY OF THE INVENTION

The object of the present invention is therefore to reach a solution where the pressure of the feed water line of a dental unit can be maintained essentially stable by using a relatively simple construction and, with respect to automatic control engineering, components of reasonable prize. Especially the object of the preferable embodiments of the invention is to realize such a construction in a way which enables, on one hand, separating of the water lines from the water system according to the orders of the authorities in order to prevent the water flowing back to the water system, and at the same time, on the other hand, allowing simple modification of the construction to be applicable for different ways and modes of use, in case so desired. As examples of the variability can be mentioned the aim to be able to use the same basic construction, despite whether water from the water system or bottled water is used as feed water, and the ease of alternating of the construction between use and cleaning modes.

The objects as mentioned above can be reached with solutions the essential features of which being defined in following patent claims, especially in characterizing parts of the independent claims. It is thus essential for the invention that there is arranged a pressure chamber to the feed water line of a dental unit, the said pressure chamber being arranged in functional connection with pressure control means, and upstream of the said pressure chamber a pump, which is arranged to be able to pump water to the said pressure chamber also when it is pressurized. The pump can be arranged to suck water e.g. from a reservoir basin physically separated from the water system. The pressure control means according to a particularly preferable embodiment of the invention comprise a valve arrangement with help of which it is possible to both lead air into the said pressure chamber in order to pressurize it and to purge air out of the chamber. In one preferable embodiment of the invention the pressure chamber is arranged detachably connectable to the feed water line, whereupon it may be detached and filled e.g. with water line detergent or replaced by a new chamber containing cleaning chemical and/or purified water, if desired. In this kind of an embodiment of the invention, where the cleaning chemical is fed into the feed water line from a pressure chamber located downstream of the pump, it is essential in view of cleaning of the water lines that there is arranged downstream of the pressure chamber a branch line leading upstream of the pump, e.g. to the previously mentioned reservoir basin.

BRIEF DESCRIPTION OF THE FIGURES

In the following the invention is described by referring to the attached drawings, in which context some preferable embodiments of the invention described above, and some others, too, are presented in more detail, of which drawings

PREFERABLE EMBODIMENTS OF THE INVENTION

Figure 1:
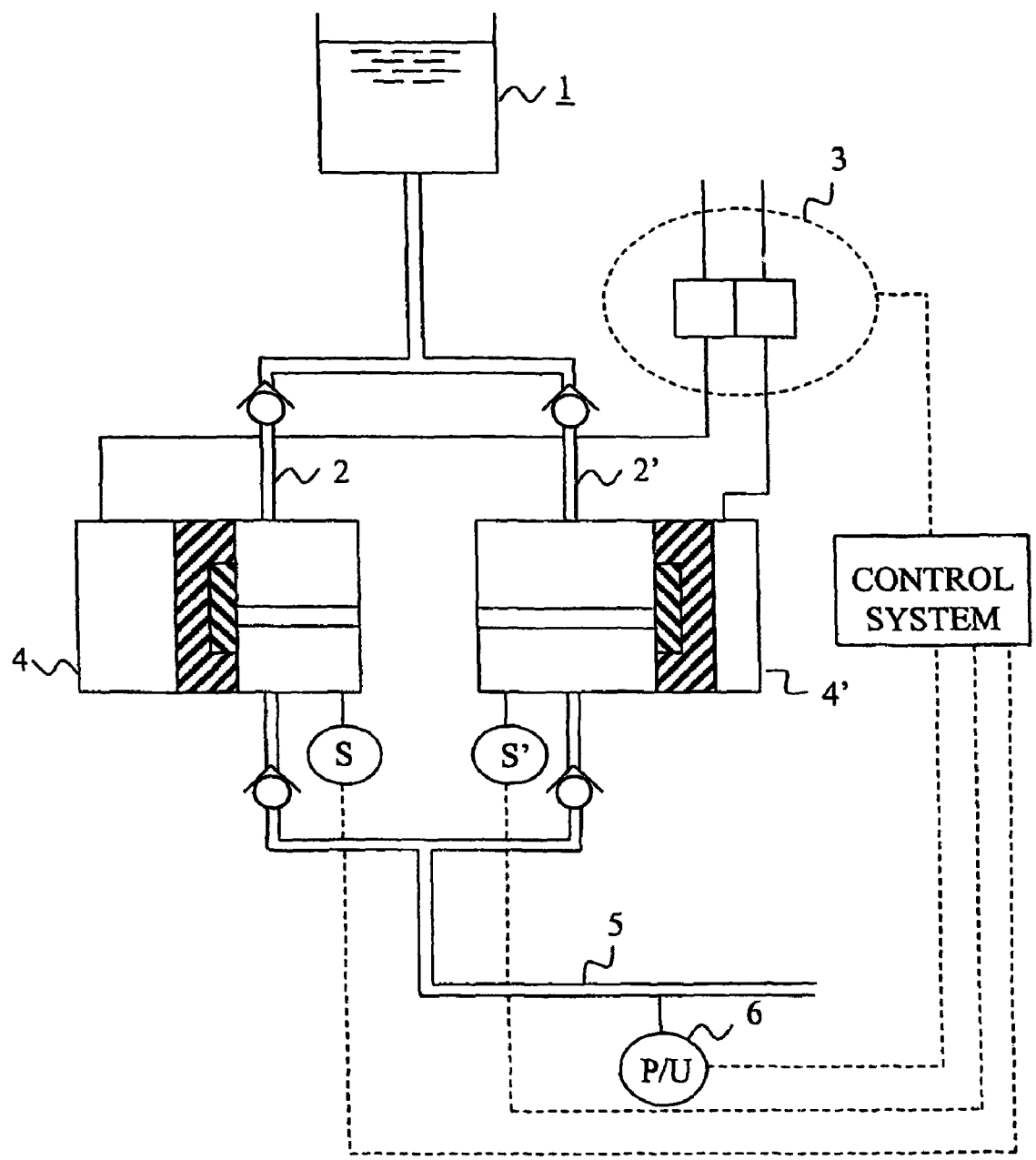
FIG. 1 presents a principle of one water feed arrangement according to prior art technology.

A water feed arrangement according to prior art technology, presented as simplified in FIG. 1, comprises a reservoir basin 1 separated from the public water system, from which basin 1 water is led via two suction lines 2, 2' to two piston pumps 4, 4', which are used pneumatically 3 and in parallel. FIG. 1 does not present all the details of the arrangement in question, which details described more precisely e.g. in the above-mentioned EP patent publication 0 524 344 B2, but it is essential in that solution to control function of the pumps 4, 4' used in parallel in such a way that their mutual function is asyncronic, guided by control signal or signals being received from pressure measuring elements 6 generally placed in the feed water line 5 on one hand, and from the observation of the operation stages S, S' of the pumps 4, 4' on the other.

Figure 2:
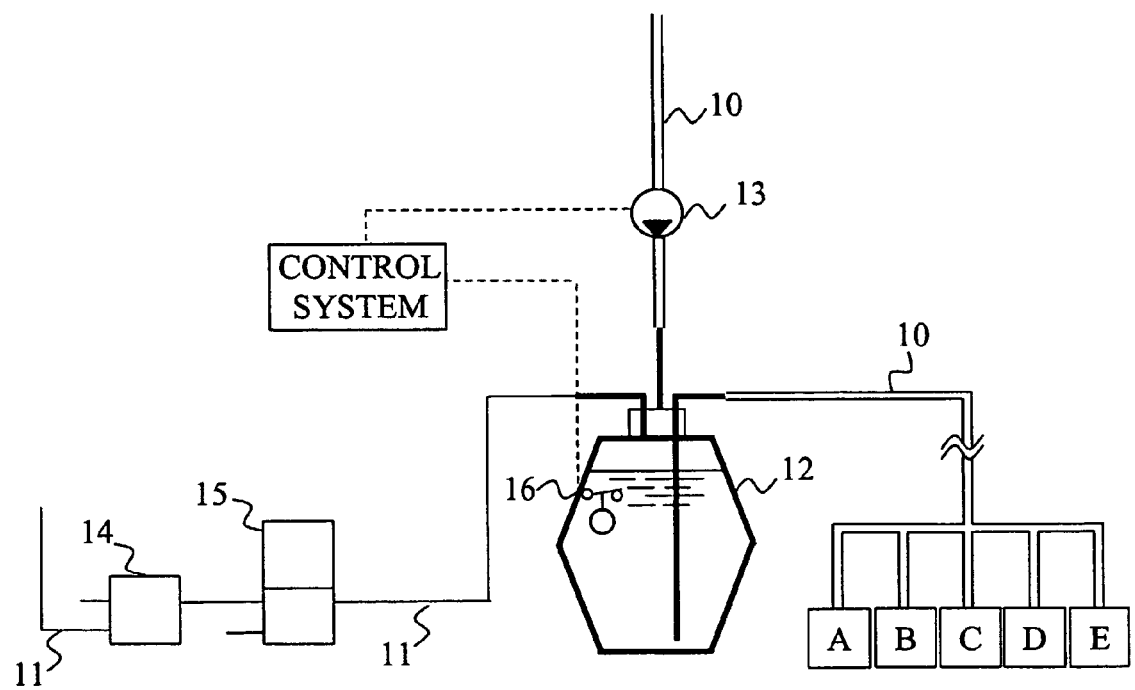
FIG. 2 presents the most essential features of a water feed arrangement according to the invention and FIG. 3 presents one preferable embodiment of the water feed arrangement according to the invention, in which the water feed link of the public water system is physically separated from the water feed line of <dental unit.

FIG. 2 presents the basic principle of a water feed arrangement according to the invention by one of its preferable embodiments, where there has been arranged in the feed water line 10, upstream of the points of use of water A, B, C, . . . , a pressure chamber 12—with its pressure control means 14, 15—in connection with a compressed air line 11, and upstream of the pressure chamber 12 a pump 13. In this context the pump means any customary pump commercially available, such as a diaphragm, a timing wheel, a centrifuge, a screw, a blade, a piston and a peristaltic pump. Pressure of the line leading to the water outlet points A, B, C, . . . of the feed water line 10 is controlled with help of the pressure chamber 12 functioning as a pressure battery and the pressure controller 14, while the pump 13 of the arrangement is arranged being able to pump water to the pressure chamber 12 also against pressure prevailing therein, in case necessary.

In an arrangement according to one preferable embodiment of the invention of FIG. 2, the pressure control is realized with a pressure controller 14 and a three-way valve 15 arranged in the compressed air line 11 of the dental unit. When the three-way valve 15 is in a position where the compressed air line 11 is in connection with the pressure chamber 12, the pressure controller 14 keeps the gas phase of the pressure chamber 12 essentially at the desired pressure regardless of the volume of the liquid phase in the pressure chamber 12 as such, and regardless of the changes of it e.g. while filling the pressure chamber 12 by letting a required amount of air out of the pressure chamber. Thanks to the arrangement according to the invention, the possible pressure fluctuations at the points of use of water A, B, C, . . . of the dental unit will be so small that a person operating the unit cannot even notice them, since the changes of volume of the phases in the pressure chamber 12 caused by the flows at the water outlet points are in any case always relatively small as compared to the total volumes of the phases in the pressure chamber 12. Therefore it is not necessary to use the most refined and thus expensive pressure controllers 14 in the arrangement according to the invention. From the point of view of the invention it is not essential whether e.g. valve 15 is operated manually or by the control system of the dental unit, or whether the pressure controller 14 functions guided by a control signal from a pressure sensor located in the feed water line 10 or in the pressure chamber 12 or independently.

The three-way valve 15 of the arrangement according to FIG. 2 can be turned to a position where it breaks off the connection between the pressure chamber 12 and the compressed air line 11 and connects the pressure chamber 12 e.g. to atmospheric pressure. The utilizing of this feature of the arrangement in some preferable embodiments of the invention is described more precisely later. The pressure control arrangement according to the invention does not necessarily have to be by detail precisely according to the one presented in FIG. 2, but the pressure control can be realized also by other means obvious to a man skilled in the art within the scope of the basic idea of the invention. Preferably, however, the arrangement includes a three-way valve 15 or an equivalent component in the compressed air line 11 arranged in functional connection with the pressure chamber 12, through which the pressure chamber 12 may be both kept in connection with the compressed air line 11 and this connection be broken off, in case desired, and a new connection opened to another pressure, such as atmospheric pressure.

The most preferable way of implementing the invention partially always depends on the relation of the typical momentary maximal water consumption of the unit in question to the capacity of the pressure chamber 12 connected to the construction. From the point of view of keeping the pressure as stable as possible, it would be most advantageous to keep the volume of the gas phase in the pressure chamber 12 as high as possible. In an operation mode of a dental unit a momentary water consumption may be so high with respect to the capacity of the pressure chamber, however, that in case the surface level in the chamber was low, the amount of water acutely available would not necessarily always be enough to meet the momentary water consumption without feed-pumping of compensatory water. From this point of view it may be of more advantage in some applications to keep the fluid level in the pressure chamber 12 at a relatively high level.

Control of height of the fluid level in the pressure chamber 12 may be realized in many different ways, e.g. by always triggering filling upon sensing of a set minimum fluid level or after having gone below the set limit value and by continuing filling either until a set maximum level has been reached or according to a standardised chamber filling pumping operation, by starting the filling always when water is consumpted at a water outlet point A, B, C, . . . and continuing until a set maximum level is sensed or e.g. by aiming to keep the level constant, e.g. with help of continuous fluid level sensing or measuring the flux running off to consumption from the pressure chamber 12—or in some combination of these. In FIG. 2 there is presented as an example a surface level sensor 16, which observes reaching of the minimum surface level and sends a control signal for starting up the pump 13.

As far as arranging pumping, i.e. replacing the water consumed at the points of use of water A, B, C, . . . in the pressure r 12 is concerned, an embodiment of the construction according to the invention regarded most preferable comprises keeping the feed water line 10 located downstream of the pressure chamber 12 constantly pressurized in the desired pressure while the dental unit is in the use-mode. The arrangement according to the invention as such for sure also enables such an operation where the feed water line 10 will be pressurized always when water consumption at the water outlet points A, B, C, . . . begins, but the construction according to the invention is preferably used particularly by seeking to keep the pressure in the pressure chamber continuously at a desired value, i.e. also when water is not consumed at the water outlet points, while the pressure chamber 12 is filled and also after the fluid level in the pressure chamber 12 has reached its desired set limit value.

Naturally it is also possible to arrange various operations to the control system of the dental unit for special or exceptional situations, such as e.g. a short-term fall of pressure in the pressure chamber 12 in a situation where the water level in the pressure chamber 12 is low and momentary water consumption is high e.g. in a water point of use "cup filling". With such a lowering of the pressure in the pressure chamber 12 it is possible to increase the water flux pumped with the pump 13 located upstream of the pressure chamber 12, whereby emptying of it can be prevented.

Naturally development of e.g. the potential problematic situation as described above as an example may be prevented already beforehand, in case so desired, by e.g. dimensioning the pump 13 of the arrangement, or by arranging the system in some other way such that water consumption at the water outlet points A, B, C, . . . can in no circumstances be higher than the maximum flux that can be pumped to the pressure chamber 12. On the other hand, development of these kind of problematic situations may also be prevented by keeping the normal fluid level in the pressure chamber 12 relatively high and by arranging the maximum pumping capacity of the pump 13 higher than at least the typical maximum water consumption over a longer period of time, whereby the short-term peaks of the water consumption that are above the average can be covered with the amount of water ready for use in the pressure chamber 12. According to the invention it is essential, however, that the pump 13 is able, when necessary, to pump water to the pressure chamber 12 also when the pressure chamber 12 is pressurized. If the pressure chamber 12 is kept continuously e.g. at 3 bar pressure it is necessary to be able to reach in practise e.g. ca. 4 bar pressure with the pump 13 for creating a flux of practical magnitude, e.g. 300 ml/min. By generalizing it can be said that an essential part of an arrangement according to the invention is a pump 13 by which a pressure of at least ca. 1 bar higher can be reached than the pressure which, in normal conditions, is meant to be kept as constant in the pressure chamber 12 or which is arranged in the pressure chamber 12.

Figure 3:
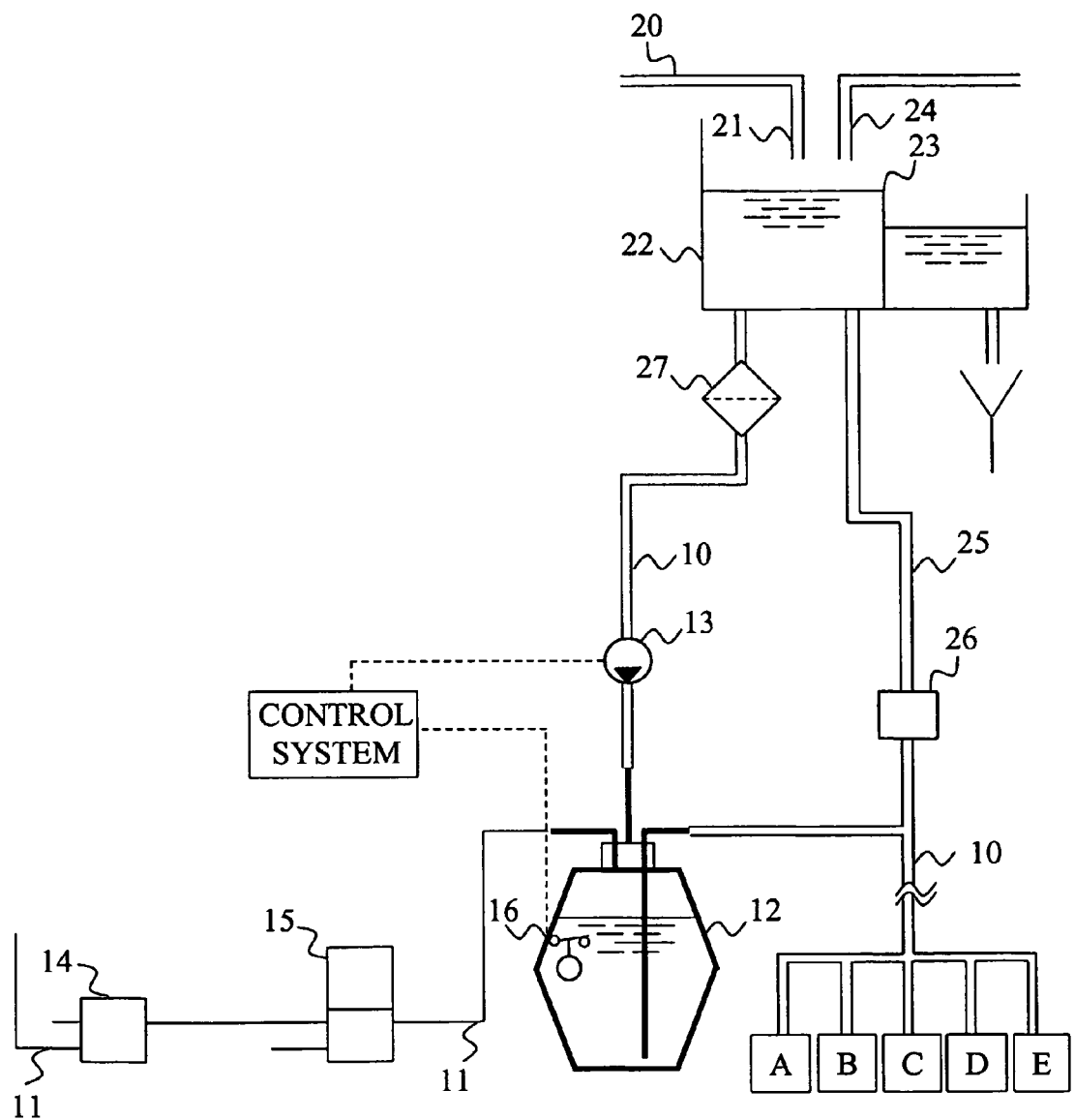

FIG. 3 presents adaptation of the water feed arrangement according to the invention to a construction where water taken from a public water system 20 is used in such a way that the water feed link 21 is physically separated from the water system of the unit itself. In that case, upstream of the pump 13 there has been arranged a basin 22, which is in contact with atmospheric pressure and acts as a storage space for feed water, the water feed link 21 of the water system 20 being placed preferably above the basin 22. In the basin 22 there has been arranged an overflow edge 23 to ensure that fluid level in the basin cannot rise closer to the water feed link 21 than desired. This way e.g. an air gap of 20 cm between the maximum fluid level in the basin and the water feed link 21 of the water system required by some authorities ensures that contaminants being possibly carried to the unit e.g. via dental instruments can in no circumstances flow back to the public water system 20. In order to protect the water system of the unit itself from external contaminants, in this kind of solutions there is typically arranged in the feed water line 10 a filter 27, preferably as close as possible to the connection from which the external water is taken to the system.

In order to clean the water system of a dental unit according to FIG. 3, the cleaning chemical can be fed e.g. to the reservoir basin 22 of the feed water, e.g. via a fixed chemical feed link 24 arranged in connection to the basin. However, one preferable embodiment of the invention comprises an arrangement where cleaning chemical is fed to the arrangement via pressure chamber 12. A feed link for the cleaning chemical (not shown in the figures) may be arranged to the pressure chamber 12, but preferably the pressure chamber 12 is arranged detachably connectable to the feed water line 10. This way the pressure chamber 12 can be detached and filled with cleaning chemical, or another pressure chamber reserved for cleaning chemical use can be utilised. In this kind of an embodiment of the invention, for example a three-way valve 15 located in the compressed air line 11 can be used for purging the pressure of the pressure chamber 12 before disconnecting it from the feed water line 10 by shutting off its connection to the compressed air line 11 and opening connection to atmospheric pressure.

An embodiment of to the invention as according to FIG. 3, in which cleaning chemical is fed to the feed water line 10 from the pressure chamber 12, essentially includes a line 25 branching off downstream of the pressure chamber 12 and leading e.g. to the feed water basin 22, into which line a valve 26 is arranged through which the water lines located upstream of the pressure chamber 12, together with the reservoir basin 22 itself and the pump 13, will be included in the chemical treatment circuit. In practise the water lines of a dental unit are thus cleaned e.g. by lowering the pressure in the pressure chamber 12 to atmospheric pressure, with the help of the three-way valve 15 as described above, whereby the pressure chamber 12 may be detached and replaced with a chamber containing detergent, or be filled with detergent. A non-return valve (not shown in the figures) is preferably arranged in the water line 10 downstream of the pressure chamber 12. The feed water line 10 is repressurized by turning the three-way valve 15 back to the position which connects the pressure chamber 12 to the compressed air line 11 and by filling the lines leading to the points of use of water A, B, C, . . . with detergent. If the arrangement includes a reservoir basin 22 and a branch line 25 leading to it, a valve 26 arranged in the branch line 25 can be kept closed at this stage. Ensuring that the lines leading to the water outlet points A, B, C, . . . have been filled with detergent may be done in any previously known manner, such as by measuring the concentration of detergent, by closing the valves of various water outlet points after a feeding time or amount of detergent set before-hand, or after it has been recognized at a water outlet point that no water but detergent runs out thereof. Finally the valve 26 of the branch line 25 is opened, the pump 13 is started and the detergent circulated through the reservoir basin 22 a time long enough in order to accomplish the needed detergent concentration also in the reservoir basin 22 and in the suction line of the pump 13. In case so desired, the reservoir basin 22 may also be emptied before starting of the cleaning cycle. The detergent is let to act in the water lines a desired time after which it is driven out of the lines and the lines are rinsed, after which the dental unit will be again ready for use.

Arranging the pressure chamber 12 as detachably attached enables adapting the arrangement according to the invention easily for a so-called clean water use as well. This is done simply e.g. by filling the pressure chamber 12 with water purified outside the system, switching the pump 13 functionally off the arrangement and feeding water from the pressure chamber 12 to the feed water line 10 under control of the pressure control means 14, 15 of the pressure chamber.

The basic solution according to the invention can be implemented also in other ways than the ones described above. For example, if directions of the authorities allow, the reservoir basin 22 does not have to be a space at least partly open and in connection to atmospheric pressure as described above, but it may also be a closed chamber. Such a reservoir chamber can be in connection to a public water system and possibly also have a link for feeding the cleaning chemical, or it can be arranged e.g. to be detachably attached, independently usable unit in a similar way as described above regarding the pressure chamber, whereby such a reservoir chamber can be used in a similar way as a reservoir/feeding chamber for water decontaminated outside the system and/or for cleaning chemical. Essential for all the embodiments of the invention are, however, the features defined in the following independent patent claims.

The invention claimed is:

1. A dental unit, comprising:
    a feed water line for leading water to at least one water outlet point or water-consuming instrument of the dental unit;
    a pressure chamber in connection with the feed water line and with a compressed air line;
    a pressure control device configured to control pressure in the pressure chamber according to a desired pressure level via the compressed air line; and
    a pump arranged along the feed water line upstream of the pressure chamber and configured to pump water to said pressure chamber when the pressure in the pressure chamber is greater than a pressure in the feed water line upstream of the pressure chamber, and
    wherein the pressure chamber is arranged within the dental unit to, during operation of the dental unit, control a prevailing pressure at a location in the feed water line downstream of the pressure chamber at which the feed water line provides water to the at least one water outlet point or water-consuming instrument.

2. The dental unit according to claim 1, wherein said pressure control device comprises a valve arrangement configured to enable pressurizing air to enter the pressure chamber and to enable air to be purged from the pressure chamber.

3. The dental unit according to claim 2, wherein said valve arrangement comprises at least one three-way valve arranged in the compressed air line, wherein the at least one three-way valve is operable to provide a connection between the pressure chamber and the compressed air line in a first state to enable pressurizing air to enter the pressure chamber, and wherein the at least one three-way valve is operable to prevent the connection between the pressure chamber and the compressed air line in a second state to connect the pressure chamber to an external pressure.

4. The dental unit according to claim 1, further comprising means for recognizing fluid level height, the means for recognizing fluid level height being arranged in the pressure chamber.

5. The dental unit according to claim 4, wherein said pump is configured to pump water to the pressure chamber periodically in accordance with adjustment signals received from the means for recognizing fluid level height of the pressure chamber.

6. The dental unit according to claim 1, further comprising a reservoir chamber arranged in the feed water line upstream of said pump and configured to store water for said pump.

7. The dental unit according to claim 6, further comprising an overflow edge structure arranged in said reservoir chamber, the overflow edge structure being configured to ensure that a fluid level in the reservoir chamber does not exceed a predetermined height threshold.

8. The dental unit according to claim 7, wherein the reservoir chamber is formed to be at least partially open to atmospheric pressure.

9. The dental unit according to claim 8, wherein a feed link connected to an external water source is arranged to feed water to the reservoir chamber from a distance above the predetermined height threshold for the fluid level in the reservoir chamber.

10. The dental unit according to claim 8, wherein a detergent feed link is arranged to feed a cleaning chemical to the reservoir chamber from a distance above the predetermined height threshold for the fluid level in the reservoir chamber.

11. The dental unit according to claim 6, further comprising a branch line arranged in the feed water line downstream of the pressure chamber leading to said reservoir chamber via which line fluid can be circulated from the pressure chamber to the reservoir chamber.

12. The dental unit according to claim 1, wherein the pressure chamber is configured to be detachably attachable to the feed water line.

13. The dental unit according to claim 1, further comprising a closable feed opening arranged in the pressure chamber for feeding detergent into the pressure chamber.

14. A method for feeding water in a dental unit, the method comprising:
    leading water to at least one water outlet point or water-consuming instrument of the dental unit using a feed water line; and
    using a pressure chamber connected with the feed water line to control a prevailing pressure at a location in the feed water line downstream of the pressure chamber at which the feed water line provides water to the at least one water outlet point or water-consuming instrument, and
    wherein using the pressure chamber connected with the feed water line to control the prevailing pressure in the feed water line downstream of the pressure chamber includes:
        using a pressure control device to control pressure in the pressure chamber according to a desired pressure level via a compressed air line connected with the pressure chamber; and
        when the pressure in the pressure chamber is greater than a pressure in the feed water line upstream of the pressure chamber, pumping water to the pressure chamber using a pump arranged along the feed water line upstream of the pressure chamber to replace water led from the pressure chamber to the at least one water outlet point or water-consuming instrument of the dental unit using the feed water line.

15. The method according to claim 14, wherein controlling pressure in the pressure chamber via the compressed air line comprises enabling pressurizing air to enter the pressure chamber and enabling air to be purged from the pressure chamber.

16. The method according to claim 15, wherein the pressure control device includes at least one three-way valve arranged in the compressed air line, wherein the at least one three-way valve is operable to provide a connection between the pressure chamber and the compressed air line in a first state to enable pressurizing air to enter the pressure chamber, and wherein the at least one three-way valve is operable to prevent the connection between the pressure chamber and the compressed air line in a second state to connect the pressure chamber to an external pressure.

17. The method according to claim 14, further comprising recognizing fluid level height in the pressure chamber and pumping water to the pressure chamber using the pump upon detection of the fluid level height being at or below a predetermined limit.

18. The method according to claim 14, further comprising storing feed water for the pump in a reservoir chamber arranged in the feed water line upstream of the pump.

19. The method according to claim 18, wherein the reservoir chamber is formed to be at least partially open to atmospheric pressure, and further comprising ensuring that a fluid level in the reservoir chamber does not exceed a predetermined height threshold using an overflow edge structure arranged in the reservoir chamber, and feeding water to the reservoir chamber from a distance above the predetermined height threshold for the fluid level in the reservoir chamber using a water feed link connected to an external water source.

20. The method according to claim 19, wherein water from a public water system is fed via the water feed link.

21. The method according to claim 19, further comprising using a detergent feed link to feed a cleaning chemical to the reservoir chamber.

22. The method according to claim 18, further comprising circulating fluid from the pressure chamber to the reservoir chamber via a branch line arranged in the feed water line downstream of the pressure chamber leading to the reservoir chamber.

23. The method according to claim 14, wherein the pressure chamber is configured to be detachably attachable to the dental unit to be filled with a cleaning chemical or purified water, or to be replaced with another suitable chamber.

24. The method according to claim 14, further comprising, upon the pressure chamber being filled with a cleaning chemical or replaced with a second chamber containing the cleaning chemical, pressurizing the pressure chamber and driving the cleaning chemical to the feed water line.

* * * * *